US00PP10012P

United States Patent [19]

Lemon

[11] Patent Number: Plant 10,012

[45] Date of Patent: Aug. 26, 1997

[54] VARIETY OF GERANIUM PLANT NAMED 'ANGEL'

[75] Inventor: David Lemon, Lompoc, Calif.

[73] Assignee: John Bodger and Sons Company, South El Monte, Calif.

[21] Appl. No.: 571,171

[22] Filed: Dec. 12, 1995

[51] Int. Cl.[6] ..... A01H 5/00

[52] U.S. Cl. ..... Plt./87.12

[58] Field of Search ..... Plt./87.12

[56] References Cited

U.S. PATENT DOCUMENTS

P.P. 3,173 5/1972 Knicely et al. ..... Plt./87.12
P.P. 7,392 12/1990 Schumann ..... Plt./87.12

*Primary Examiner*—Howard J. Locker

[57] ABSTRACT

The cultivar is characterized by its white color. Its compact, controlled growth habit and prolific blooms provide for superb cuttings and performs equally well in hanging baskets or in a ground bed. The blooms are heat tolerant.

1 Drawing Sheet

BACKGROUND OF THE NEW PLANT

The present invention comprises a new and distinct cultivar of *Pelargonium×hortorum* known by the varietal name Angel (Oglevee No. 75, Bodger No. 10GM 148-1). The new variety was discovered in a selective breeding program by David Lemon at Bodger Seeds, Ltd., Lompoc, Calif. The new variety is a selection from the crossing of Fisbal (U.S. Plant Pat. No. 7,392)×Snowhite (U.S. Plant Pat. No. 5,312). Both Fisbal and Snowhite have a semi-double flower form, whereas the flower form for Angel is double. Angel blooms early, whereas Fisbal blooms later. Angel is more heat tolerant than Snowhite.

The new cultivar was first asexually reproduced by cuttings at Oglevee Ltd., Connellsville, Pa., and has been repeatedly asexually reproduced by cuttings at Oglevee Ltd. in Connellsville, Pa. It has been found to retain its distinctive characteristics through successive propagations.

The new cultivar, when grown in a glass greenhouse in Connellsville, Pa., using full light, 60° fahrenheit night temperature, 72° fahrenheit day temperature, 72° fahrenheit vent temperature and grown in a soilless media of constant fertilizer 200 parts per million of nitrogen and potassium has a response time of six weeks from the rooted cutting to a flowering plant in a 10.0 cm pot.

DESCRIPTION OF THE DRAWING

The accompanying drawing illustrates the new cultivar, the color being as nearly true as possible with color illustrations of this type.

DESCRIPTION OF THE NEW PLANT

The following detailed description sets forth characteristics of the new cultivar. The data which defines each characteristic was collected from asexual reproductions carried out by Oglevee Ltd. in Connellsville, Pa. The plant histories were taken on rooted cuttings potted on Feb. 15, 1995 and flowered Apr. 1, 1995 under full light and greenhouse, and colorings were taken indoors under 200–220 foot candles of fluorescent cool white light using the R.H.S. Colour Chart of The Royal Horticultural Society of London.

THE PLANT

Classification:

*Botanical.*—*Pelargonium×hortorum.*

Form: Semi-dwarf mound.

*Height.*—16.0–19.0 cm from the media surface.

*Growth.*—Controlled medium habit; free basal branching; free and early flowering with semi-double bloom.

*Strength.*—Free standing; more soluble salts tolerant than other white varieties, large medium green foliage.

Foliage: Stalked leaf attachment.

Leaves:

*Size.*—10.0–12.0 cm across.

*Shape.*—Reniform; cordate base.

*Margin.*—Crenate.

*Texture.*—Leathery pubescent.

*Color.*—Top: Green Group 137D; Zone: Not present. Bottom: Green Group 138B.

*Ribs and veins.*—Palmate venation: Color: Green Group 137D.

Petioles:

*Length.*—4.5–6.0 cm.

*Color.*—Yellow/Green Group 146C.

Stem:

*Color.*—Yellow/Green Group 146C.

*Internodes.*—1.5–3.5 cm in length.

THE BUD

Shape: Upright; hemispherical cluster.

Size: 2.5–3.5 cm across.

INFLORESCENCE

Blooming habit: Semi-double; free and early flowering; slow to shatter.

Size: 8.0–10.0 cm across.

Borne: Umbel; florets on pedicel; pedicel on peduncle; 10.0–13.0 cm above foliage.

Florets:

*Closed.*—Bud size: 1.0–1.5 cm; bud showing the faintest tint of color.

*Open.*—Form — Slightly cupped; semi-double.

*Number.*—About 57 florets per inflorescence.

*Color.*—Top: White Group 155D Bottom: White Group 155D.

*Petals.*—5–6 in number; separate, not united; margin entire; obovate; flat to slightly cupped.

*Size.*—3.5–4.5 cm.

*Texture and appearance.*—Smooth, slightly reflective; appearance from a distance is a bright, clean, white flower above medium green foliage.

Petaloids:
*Quantity.*—1–3.
*Shape.*—Narrow, twisted, some fused to filaments.
*Color.*—Top: White Group 155D; Bottom: White Group 155D.
Pedicel:
*Length.*—2.5–3.5 cm.
*Color.*—Green Group 137D.
Peduncle: Thick and strong.
*Length.*—13.0–19.0 cm in length.
*Color.*—Yellow-Green 146C.
Persistence:
*Disease resistance.*—Not known.
*Lasting quality.*—*Not known.*

REPRODUCTIVE ORGANS

Stamens:
*Anthers.*—1.0–2.0 mm in length.
*Filaments.*—5.5–6.5 mm in length; white.
*Pollen.*—Light golden brown.
Pistils:
*Number.*—One.
*Length.*—6.0–7.5 mm.
*Stigma.*—4-parted, green color.
*Style.*—2.0 mm, green color.
Ovaries: Superior, pubescent; pale green in color, 3.5–5.0 mm in length.
Fruit: None observed.

GENERAL CHARACTERISTICS

Angel is a unique new white geranium variety. It is similar in size to Sincerity (unpatented) and Wendy Ann (unpatented). This variety is more tolerant to soluble salts than other white varieties such as Snowmass (U.S. Plant Pat. No. 3,173) or Snowhite, currently on the market. Sincerity is distinguished from Angel by its scarlet colored flower, and dark zonation on its leaves. Wendy Ann is distinguished from Angel by its scarlet pink flower and medium zone. Snowmass is distinguished from Angel by its later blooming time and less vigourous growth habit. Because Angel has a relatively high tolerance to soluble salts, more fertilizer can be applied to Angel than other varieties, resulting in more rapid growth without damage to the plant, and resulting in a darker leaf color. Along with the strong growth habit, Angel is also a good cutting producer through basal branching, it roots with ease and speed, is very heat tolerant in the outdoor garden and very free flowering.

I claim:

1. A new and distinct variety of Geranium plant, substantially as shown and described.

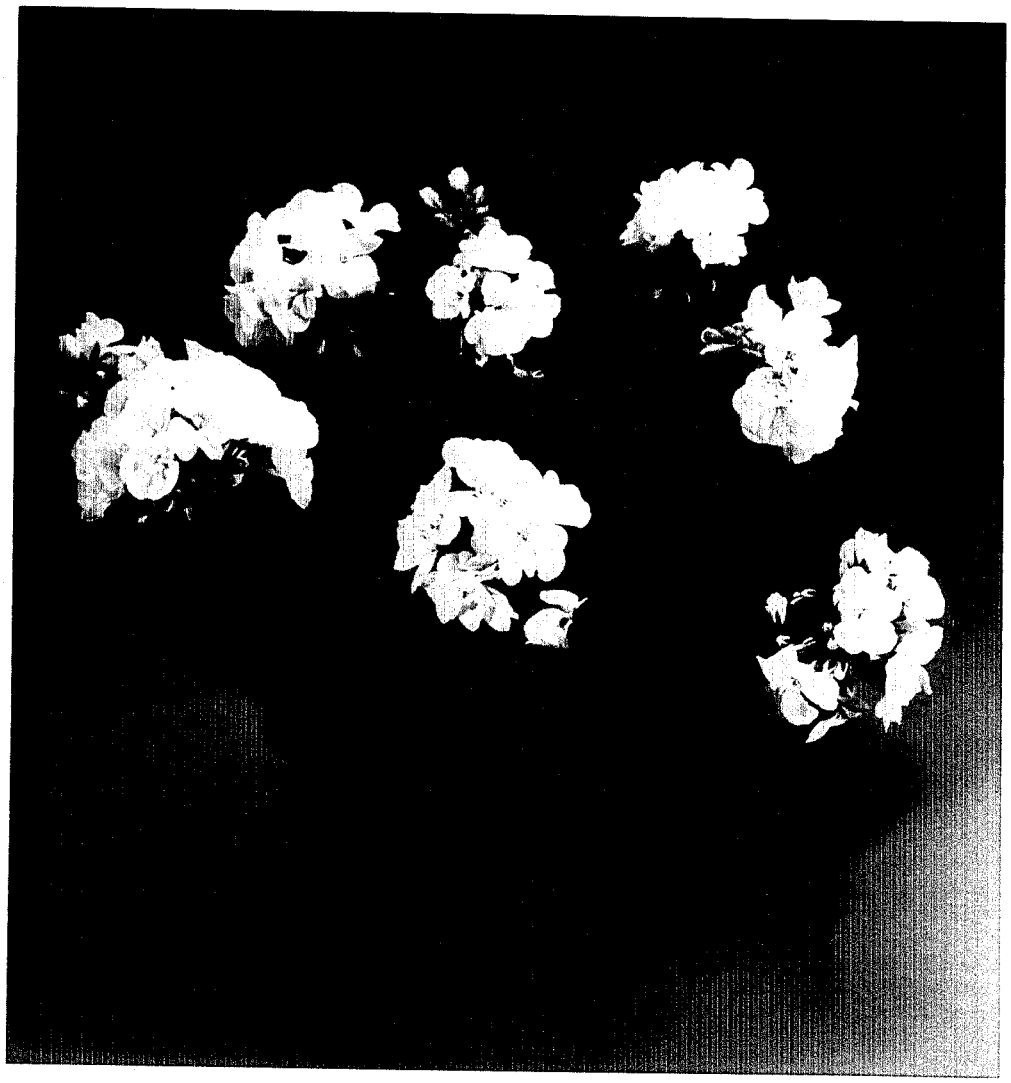

* * * * *